United States Patent [19]

Prince

[11] 4,168,465
[45] Sep. 18, 1979

[54] TAPERED HOLE CAPACITIVE PROBE

[75] Inventor: Morris D. Prince, Atlanta, Ga.

[73] Assignee: The United States of America as represented by the Secretary of the Air Force, Washington, D.C.

[21] Appl. No.: 861,083

[22] Filed: Dec. 15, 1977

[51] Int. Cl.² .......................................... G01R 27/26
[52] U.S. Cl. .................................................. 324/61 P
[58] Field of Search ............................ 324/61 P, 61 R

[56] References Cited

U.S. PATENT DOCUMENTS

| 2,417,062 | 3/1947 | Coake | 324/61 P |
|---|---|---|---|
| 3,426,272 | 2/1969 | Griffin | 324/61 P |
| 4,112,355 | 9/1978 | Gibson, Jr. et al. | 324/57 R |

Primary Examiner—Stanley T. Krawczewicz
Attorney, Agent, or Firm—Joseph E. Rusz; Henry S. Miller

[57] ABSTRACT

A tapered capacitive probe embodies vertical stripes for detecting irregular flaws in metal holes. Horizontal stripes are added to the probe and connected in a one-to-one relationship with the vertical stripes to detect and measure flaws with angular uniformity. Invention allows flaws to be detected in vertical, horizontal or angular direction and discloses approximate shapes and locations.

3 Claims, 1 Drawing Figure

U.S. Patent
Sep. 18, 1979
4,168,465
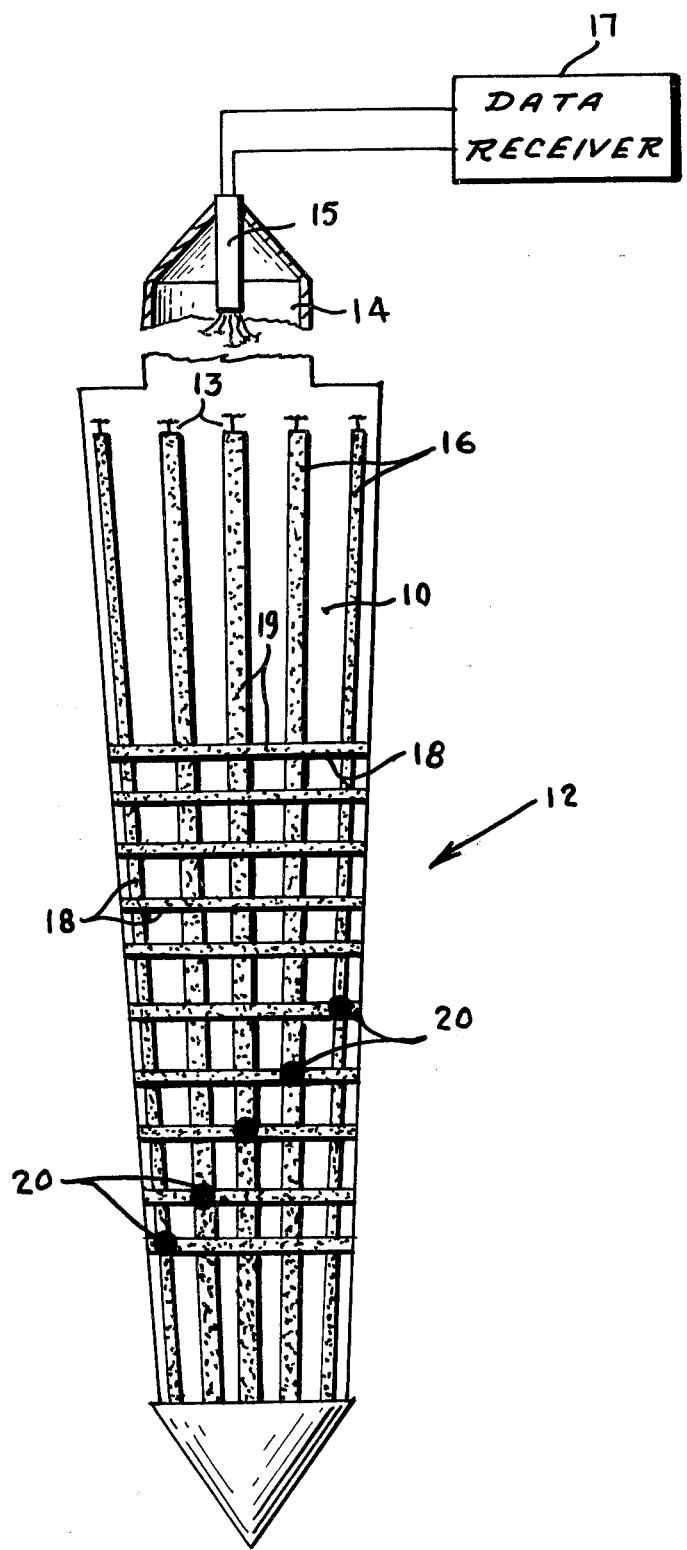

TAPERED HOLE CAPACITIVE PROBE

STATEMENT OF GOVERNMENT INTEREST

The invention described herein may be manufactured and used by or for the Government for governmental purposes without the payment of any royalty thereon.

BACKGROUND OF THE INVENTION

This invention relates generally to the non-destructive testing of tapered fastner holes, and more specifically to an improved capacitive probe for detecting flaws in such holes.

The use of capacitive probes in inspecting holes for structural flaws, such as cracks, is not new to the art. Earlier probes with only vertical segments were inserted by hand, removed, turned, and reinserted in the hold; a meter, connected to the probe and measuring capacitance and variations therein, would fluctuate if a flaw was detected in the hole. This probe and method is fairly crude and fails to provide data sufficiently accurate for today's standards. For example, earlier probes are generally insensitive to scoring and other defects caused by drill rotation. In cases where such a flaw can be detected, the earlier probe gives no information relative to the depth of the flaw in the hole or to its vertical dimension. Hence, the distinct condition referred to in the art as "barreling" and "bell-mouthing" could show identical readings.

Furthermore, the earlier probes could not detect whether a hole was too large or too small, the indications from these defects being indistinguishable from those of various other defects.

The invention detects flaws in both the vertical and horizontal direction and discloses their approximate shapes and locations. This additional information aids in determining if the hole is satisfactory and also the cause of the flaw. The invention also measures the extent by which a hole is too large or too small by measuring the amount by which the probe protrudes above or below the work piece.

SUMMARY OF THE INVENTION

The invention involves a shaped probe for inspecting tapered fastening holes in metal or other conductive structures. For clarity of discussion, in this disclosure it is assumed that the tapered hole to be inspected is found in material, termed the work piece, which lies generally in the horizontal plane so the axis of the hole is vertical.

The probe consists of an elongated shaft tapered toward one end and provided with a handling means at the other end. The shaft is formed of an electrically insulating material. Located on the shaft are a plurality of electrically conductive vertical (longitudinal) segments (stripes) in a spaced relationship around the circumference of the shaft. These segments are connected to a capacitance measuring system of conventional design and which is currently available on the open market. It is the purpose of the capacitive measuring system to measure the capacitance between selected segments and the work piece. Also located on the shaft and overlying the vertical segments are a plurality of electrically conductive horizontal (circumferential or ring-like) segments, equal in number to the number of vertical segments.

Each of the horizontal segments is insulated from all but one of the vertical segments. That is, each horizontal segment is electrically connected to one and only one vertical segment. Segments are connected sequentially from bottom to top and, say, left to right to provide an orderly basis on which to analyze the data received therefrom.

This invention disclosure describes a tapered probe with vertical and horizontal segments connected together in an orderly one-to-one basis. A more general embodiment of the invention consists of a plurality of sequential segments of one design, an equal number of sequential segments of a second design, the segments of the first design being connected to the segments of the second design, the segments of the first design being connected to the segments of the second design on an orderly one-to-one basis. The design of the segment shapes is determined by the specified pattern of the flaws to be detected.

It is therefore an object of the invention to provide a new and improved tapered hole capacitive probe.

It is another object of the invention to provide a new and improved tapered hole capacitive probe that detects flaws in both vertical and horizontal directions.

It is a further object of the invention to provide a new and improved capacitative probe that detects flaws in an antular direction and provides information on their shape and location.

It is still another object of the invention to provide a new and improved capacitive probe that is more sensitive to flaws with angular uniformity.

It is another object of this invention to provide a new and improved capacitive probe which will determine the extent by which a tapered hole is too large or too small by measuring the amount by which the probe protrudes above or below the hole.

It is still a further object of the invention to provide a new and improved capacitive probe that is light in weight and easily operated.

It is another object to provide a new and improved capacitive probe that is of simple construction, reliable, low in cost, and manufactured with relative simplicity.

It is another object of this invention to provide an improved capacitive probe with a plurality of N vertical segments and an equal number of horizontal segments interconnected in a one-to-one relationship so that only N conductive leads need be connected to the date collecting and processing device.

It is another object of this invention to provide a new and improved capacitive probe that is more sensitive to flaws of a specified pattern.

These and other advantages, features, and objects of the invention will become more apparent from the following description taken in connection with the illustrative embodiment in the accompanying drawing.

DESCRIPTION OF THE DRAWING

The FIGURE is a side elevational view showing vertical and horizontal segments.

DESCFIPTION OF THE PREFERRED EMBODIMENT

Referring now to the FIGURE, the probe is formed of a base 10 having a generally cylindrical shape. The probe is tapered toward one end as shown generally at 12 to fit the particular hole it is designed to test. The probe, which is formed of an electrically insulative material has an adapter 14 which fits into a handle in the case of a hand held probe, or into a mechanical driver mechanism in the case of an automatic probe. The end of the probe nearest to the adapter 14 is the larger end and will be referred to as the handle end.

A plurality of vertical (longitudinal) electrically conductive segments 16 are affixed to the base, typically at 30° intervals around the circumference of the probe. The term "vertical segment" as used herein refers to a segment which is essentially vertical when the probe is held so that its longitudinal axis is vertical. (More precisely, a vertical segment coincides with a straight-line element of the truncated cone which is the tapered portion of the probe.) These segments are connected at the handle end by lines 13 which form cable 15 passing through handle 14 and on to data receiver 17 where the information is processed.

Positioned along the probe is a plurality of electrical segments 18 referred to as horizontal (circumferencial or ring-like) segments. The number of horizontal segments is equal to the number of vertical segments. The term "horizontal segment" as used herein refers to a ring-like segment whose axis of rotation is the longitudinal axis of the probe. All segments both vertical and horizontal, are electrically insulated from each other and from the work piece, except as noted below.

An insulating coating lies between the vertical segments 16 and the horizontal segments 18. Insulation is selectively removed at points 20, thereby providing an electrical path between sequentially located horizontal and vertical segments consisting of one vertical segment and one horizontal segment has only one point of electrical contact between the two segments of the pair. That is, vertical segment No. 1 is connected to horizontal segment No. 1, vertical segment No. 2 is connected to horizontal segment No. 2, and so forth. Further, the body of the probe including the vertical and horizontal segments is covered by an insulating coating 19 to prevent electrical contact between the segments and the work piece. It is understood that insulative coatings of high dielectric constant may be used in order to reduce the apparent thickness of the coating as measured by the capacitive measuring device.

In operation, a hole is inspected by the repeated insertion of the probe in the hole, the probe being rotated between insertions each time in the same direction and by approximately the same amount. A set of capacitive readings is taken during each insertion, reading the capacitance between each segment pair and the work piece. These readings are processed by on-line data computing methods to produce the following two sets of data: (1) The readings for each segment identified as 16 are averaged for the various insertions. Variances of these averages disclose rotational (ring-like) flaws and also the identification of the horizontal segment which coincides with the flaw and hence reveals its depth. (2) The readings for each angular position referred to the hole are averaged. Variances of these averages disclose vertical flaws, and also the angular position of the flaw. Results of the computation are presented as a simple go-no-go light on the data output device. Data are also recorded or transmitted for layer presentation to depict the shape of the hole in more detail.

The amount by which a tapered hole is too large or too small is also easily measured by determining the distance by which the probe protrudes above or below the hole. This is readily accomplished since horizontal segments on the protruding portion of the probe have very low capacitive readings.

It is understood that the repeated insertion of the probe is a useful technique for averaging out any dissimilarities in the vertical segments of the probe due to manufacturing tolerances, but that data processing and pattern recognition techniques are available which yield most or all of the desired information from only one or two insertions.

It should be further understood, of course, that the foregoing disclosure relates to only a preferred embodiment of the invention and that numerous modifications of alterations may be made therein without departing from the spirit and scope of the invention as set forth in the appended claims.

What is claimed is:

1. An improved tapered hole capacitive probe comprising: A base having a long generally cylindrically shape tapering toward one end and formed of an electrically insulating material; a plurality of electrically conductive segments affixed to the base and spaced at equal distances around the circumference of the probe, each segment lying essentially parallel to the longitudinal axis of the probe, a like number of electrically conductive segments of ring-like, electrically conductive, segments affixed to the base and equally spaced along the longitudinal axis of the probe, and lying in a plane transverse to the longitudinal axis; means for electrically connecting selected parallel and transverse segments together in a sequential manner, and means for connecting said segments to a data receiving means.

2. An improved tapered hole capacitive probe according to claim 1 wherein said electrically conductive segments are insulated from all segments other than the said selected segments.

3. An improved tapered hole capacitive probe according to claim 1 wherein the number of leads required to connect said electrically conductive segments to a data receiving means is equal to one-half the total number of said segments.

* * * * *